(12) United States Patent
Zhu (10) Patent No.: US 10,517,565 B2
(45) Date of Patent: Dec. 31, 2019

(54) DUAL-PROBE IMAGING SYSTEM AND PROCESS OF USING SAME

(71) Applicant: The University of Connecticut, Farmington, CT (US)

(72) Inventor: Quing Zhu, Mansfield, CT (US)

(73) Assignee: THE UNIVERSITY OF CONNECTICUT, Farmington, CT (US)

( * ) Notice: Subject to any disclaimer, the term of this patent is extended or adjusted under 35 U.S.C. 154(b) by 1141 days.

(21) Appl. No.: 15/028,756

(22) PCT Filed: Jul. 25, 2013

(86) PCT No.: PCT/US2013/051994
§ 371 (c)(1),
(2) Date: Apr. 12, 2016

(87) PCT Pub. No.: WO2014/018728
PCT Pub. Date: Jan. 30, 2014

(65) Prior Publication Data
US 2016/0262723 A1 Sep. 15, 2016

Related U.S. Application Data

(60) Provisional application No. 61/675,457, filed on Jul. 25, 2012.

(51) Int. Cl.
*A63F 9/24* (2006.01)
*A61B 8/00* (2006.01)
(Continued)

(52) U.S. Cl.
CPC .......... *A61B 8/4416* (2013.01); *A61B 5/0073* (2013.01); *A61B 8/085* (2013.01);
(Continued)

(58) Field of Classification Search
CPC ... A61B 5/0073; A61B 8/4444; A61B 8/0825; A61B 8/4416
See application file for complete search history.

(56) References Cited

U.S. PATENT DOCUMENTS 6,181,414 B1 * 1/2001 Raz .................. G01N 15/1475
250/339.05
6,264,610 B1 * 7/2001 Zhu ...................... A61B 5/0091
600/443

(Continued)

OTHER PUBLICATIONS

Patent Cooperation Treaty, International Searching Authority, International Search Report, PCT/US2013/051994, dated Nov. 7, 2013, 7 pages.

(Continued)

*Primary Examiner* — Steve Rowland
(74) *Attorney, Agent, or Firm* — Cantor Colburn LLP (57) ABSTRACT

An imaging system includes a primary probe that includes a substrate; an ultrasound transducer disposed in the substrate to irradiate a first tissue with an ultrasound frequency; a first near infrared source to irradiate the first tissue with a first near infrared wavelength; and a first light detector to detect a first detected wavelength from the first tissue; an auxiliary probe that includes a second near infrared source configured to irradiate a second tissue with a second near infrared wavelength; and a second light detector configured to detect a second detected wavelength from the second tissue. The system also can include an optical tomography device; an ultrasound device; and a processor unit. A process for imaging includes disposing the primary probe on a first tissue, disposing an auxiliary probe on a second tissue, irradiating the first tissue, and irradiating the second tissue to produce an image of the first tissue.

23 Claims, 8 Drawing Sheets (51) Int. Cl.
  *A61B 8/08*   (2006.01)
  *A61B 5/00*   (2006.01)
  *A61B 8/14*   (2006.01)
  *A61B 90/00*  (2016.01)

(52) U.S. Cl.
  CPC .............. *A61B 8/0825* (2013.01); *A61B 8/14* (2013.01); *A61B 8/4444* (2013.01); *A61B 8/463* (2013.01); *A61B 8/5223* (2013.01); *A61B 8/5261* (2013.01); *A61B 2090/3735* (2016.02)

(56) References Cited

U.S. PATENT DOCUMENTS

| | | | |
|---|---|---|---|
| 8,070,682 B2 | 12/2011 | Zhu | |
| 2003/0144583 A1* | 7/2003 | Cheng | A61B 5/14546 600/322 |
| 2004/0039268 A1 | 2/2004 | Barbour et al. | |
| 2006/0189861 A1* | 8/2006 | Chen | A61B 5/14553 600/331 |
| 2008/0058638 A1* | 3/2008 | Zhu | A61B 5/0091 600/425 |
| 2008/0218732 A1* | 9/2008 | Mil'shtein | A61B 5/0059 356/51 |
| 2010/0160752 A1 | 6/2010 | Chance | |
| 2011/0137177 A1* | 6/2011 | Toma | A61B 5/0059 600/473 |

OTHER PUBLICATIONS

Patent Cooperation Treaty, International Searching Authority, Written Opinion, PCT/US2013/051994, dated Nov. 7, 2013, 7 pages.

* cited by examiner

DUAL-PROBE IMAGING SYSTEM AND PROCESS OF USING SAME

CROSS REFERENCE TO RELATED APPLICATIONS

This application is a National Stage application of international application number PCT/US2013/051994 filed Jul. 25, 2013, which claims the benefit of U.S. provisional application number 61/675,457 filed Jul. 25, 2012, both of which are incorporated herein by reference in their entirety.

STATEMENT REGARDING FEDERALLY SPONSORED RESEARCH

This invention was made with government support under Grant No. R01EB002136 awarded by the National Institutes of Health. The government has certain rights in the invention.

BACKGROUND

Health maintenance, disease prevention, and diagnosis are performed via various prophylactic measures and diagnostic techniques. In the case of suspected tumor appearance, a patient can be subjected to invasive surgical procedures such as a biopsy of tissue. Another, noninvasive technique is tissue imaging using an imaging modality that may or may not require placement of a device near the suspected tumor and in contact with the patient's skin.

Biological imaging of living tissue involves radiation from the X-ray region through the microwave region of the electromagnetic spectrum. Techniques such as computed tomography (CT) and magnetic resonance imaging (MRI) provide a glimpse into structural features of tissue, and mathematical processing of two-dimensional data can render three-dimensional images of such tissue. Both hard and soft tissue can be imaged. Contrast agents allow improved resolution and enhancement of images as well as a means for imaging of cavities. For example, micro bubble contrast agents have been used in echocardiograms for cardiac shunt detection.

Imaging with non-ionizing radiation is preferred due to concerns over tissue damage and health effects of ionizing radiation. Further, many practitioners and patients seek to alleviate risk factors associated with certain contrast agents. However, some widely used imaging techniques have resolution and contrast insufficient to discover lesions and tumors at the on-set of growth. The art is always receptive to materials or methods that have enhanced resolution and image quality and that are also rich in information content.

SUMMARY

Disclosed herein is an imaging system comprising: a primary probe comprising: a substrate; an ultrasound transducer disposed in the substrate to irradiate a first tissue with an ultrasound frequency; a first near infrared source disposed in the substrate to irradiate the first tissue with a first near infrared wavelength; and a first light detector disposed in the substrate to detect a first detected wavelength from the first tissue; an auxiliary probe comprising: a second near infrared source configured to irradiate a second tissue with a second near infrared wavelength; and a second light detector configured to detect a second detected wavelength from the second tissue.

Also disclosed herein is a system for imaging comprising: a primary probe to irradiate a first tissue; an auxiliary probe to irradiate a second tissue; an optical tomography device connected to the auxiliary probe and the primary probe; an ultrasound device connected to the primary probe; and a processor unit operatively connected to the optical tomography device.

Further disclosed is a process for imaging, the process comprising: disposing a primary probe on a first tissue, the primary probe comprising a first near infrared source, first light detector, and ultrasound transducer; disposing an auxiliary probe on a second tissue, the auxiliary probe comprising a second near infrared source and second light detector; irradiating the first tissue with a first near infrared wavelength and an ultrasound frequency from the primary probe; and irradiating the second tissue with a second near infrared wavelength from the auxiliary probe to produce an image of the first tissue.

The above described and other features are exemplified by the following figures and detailed description.

BRIEF DESCRIPTION OF THE DRAWINGS

Referring now to the figures, which are embodiments, and wherein like elements are numbered alike.

DETAILED DESCRIPTION

It has been found that real time imaging of biological tissue that includes an abnormality such as a lesion can be achieved by simultaneously using a (primary) probe to image the abnormality and another (auxiliary) probe to estimate and monitor an optical property change of normal tissue and to feedback information about the change to the primary probe to improve imaging quality. This technique provides rapid data processing, high imaging quality, and real-time images that include morphological and functional properties of the abnormality. The imaging system herein offers improved tissue analysis, diagnostic accuracy, and patient comfort.

In ultrasound imaging, tissue is subjected to an ultrasound frequency and an ultrasound reflection or echo from the tissue is detected. The ultrasound echo is processed to construct a tomographic image of the tissue. This method is adequate for imaging morphology of tissue. Hybrid techniques that harness ultrasound technology and another imaging modality are being investigated in laboratory and clinical studies. One such imaging modality uses diffuse near infrared radiation. A probe including an ultrasound transducer and near infrared excitation and detection optics irradiates tissue with ultrasound and near infrared radiation to produce information about morphology and vascularization of the tissue. However, the optical properties of an inclusion, e.g., a lesion or tumor, obtained from the near infrared radiation must be background-corrected in order to determine accurately these properties. In general, a background optical property of a tissue is obtained from a normal tissue without an inclusion, lesion, or tumor to allow a background correction process. To this end, the same probe is placed on normal tissue and background optical parameters are estimated from the reflected near infrared radiation. Additionally, the same probe is placed on tissue with an inclusion, lesion, or tumor to image the lesion optical properties or vascularity before or after the data collection from the normal tissue. This methodology is processor intensive and time-consuming, and not capable of tracking changes of the background properties in real-time. Thus, real time imaging is not readily achievable with this methodology. The imaging system herein decreases the processing time and increases the accuracy of mapping lesion optical properties and produces images by simultaneously using two different probes, a primary probe and an auxiliary probe. The primary probe irradiates a tissue that includes an abnormality (e.g., a lesion), and the auxiliary probe irradiates a normal tissue. The data of the normal tissue collected by the auxiliary probe is used to estimate optical parameters of the normal tissue, which is used to background-correct the optical data of the abnormal tissue collected by the primary probe. As a result, processing time is greatly reduced by using the two probes such that imaging of abnormal tissue is accomplished in real time. Additionally, the optical source and detector arrangement on the auxiliary probe allows more accurate estimation of background optical properties because there is a central source disposed in the middle of the probe.

To obtain a real time, accurate image of biological tissue, an imaging system includes a primary probe and an auxiliary probe. The primary probe includes an ultrasound transducer, first near infrared source, and first light detector disposed in a substrate. The auxiliary probe includes a second near infrared source and a second light detector. The ultrasound transducer and first near infrared source irradiate a first tissue respectively with an ultrasound frequency and a first near infrared wavelength. The first light detector detects a first detected wavelength from the first tissue. Similarly, in the auxiliary probe, the second near infrared source irradiates a second tissue with a second near infrared wavelength, and the second light detector detects a second detected wavelength from the second tissue. The first and second detected wavelengths are, e.g., scattered near infrared photons. The combination of primary and auxiliary probes provides real time imaging to be performed on biological tissue where the first tissue includes an abnormality, and the second tissue is normal tissue. The tissue can be any soft tissue including breast, axillary, abdominal, buttock, limb, lumbar, neck, facial, and the like.

Figure 1:
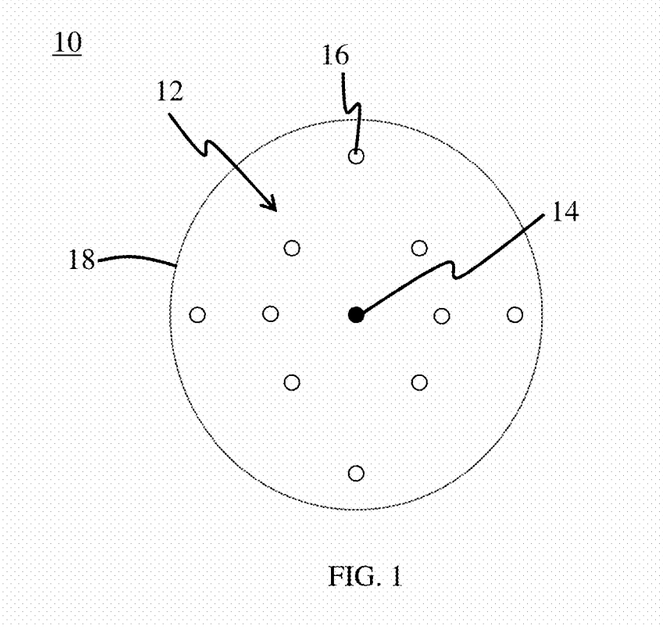
FIG. 1 shows a front view of an auxiliary probe according to an exemplary embodiment.
Figure 2:
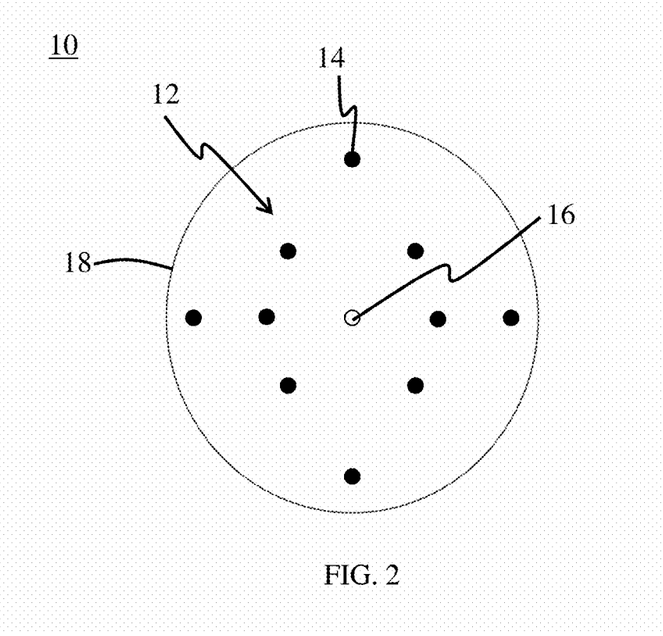
FIG. 2 shows a front view of an auxiliary probe according to an exemplary embodiment.

FIGS. 1 and 2 show front views of auxiliary probes. The auxiliary probe 10 includes a near infrared source 14 and a light detector 16 disposed as an array 12 of sources 14 and detectors 16 in a substrate 18. Near infrared wavelengths propagate from the near infrared source 14 and into tissue. Some of the near infrared light is absorbed by the tissue while some is scattered. The scattered or reflected near infrared light impinges on the light detector 16, which collects the scattered near infrared photons. The relative position, geometric pattern, and number of the near infrared source 14 and light detector 16 can determine the spatial resolution, amplitude, and phase of the detected scattered near infrared light with respect to the incident near infrared radiation from the near infrared source 16.

As shown in FIG. 1, a single near infrared source 14 is disposed among a plurality of light detectors 16. In contrast, a light detector 16 can be disposed among a plurality of near infrared sources 14 as in FIG. 2. Although a single near infrared source 14 (FIG. 1) or single light detector (FIG. 2) is illustrated, more than one can be used. Moreover, the position of a near infrared source 14 can be disposed centrally with respect to the plurality of light detectors 16, or the light detector 16 can be disposed centrally among the near infrared sources 14. The number of the near infrared sources 14 and light detectors 16 can be selected based on considerations of the illumination needed for a particular tissue and characteristics of the tissue to be irradiated such as an illumination depth of the tissue, density of the tissue, absorption property of the tissue, scattering propensity of the tissue, presence of hard tissue, concentration and type of chromophores present, and the like. The number of near infrared sources 14 can be any number effective to produce a desired illumination (pattern or intensity), e.g., from 1 to 50, specifically 1 to 20, and more specifically 1 to 10. The number of light detectors 14 can be any number effective to detect significant amounts of scattered near infrared photons for estimation of an optical property of the tissue, e.g., from 1 to 50, specifically 1 to 20, and more specifically 1 to 10. The geometric pattern of the relative position of the near infrared source 14 and light detector 16 can be that shown in FIGS. 1 and 2 and many other patterns. In an embodiment, a near infrared source 14 is interposed between at least two second light detectors 16. In another embodiment, the light detector 16 is interposed between at least two near infrared sources 14. In some embodiments, the near infrared source 14 is disposed between a majority of all of the light detectors 16. In an embodiment, the light detector 16 is disposed between a majority of all of the near infrared sources 14.

In these configurations, the light detector 16 is arranged in the auxiliary probe 10 to obtain a large solid angle subtended by the light detectors 16 for efficient detection of scattered near infrared radiation. The design of the auxiliary probe 10 allows tissue optical parameters to be determined from the detected scattered near infrared light with high efficiency and detection coverage. That is, the auxiliary probe 10 collects a substantial portion of scattered light from the tissue that propagates toward the auxiliary probe 10 without a blind spot in its field of view.

In an exemplary embodiment, a near infrared source 14 is disposed near a peripheral edge of the substrate 18 instead of near a center of the substrate 18, and a plurality of light detectors 16 are disposed at various locations on the substrate 18 so that a substantial portion of scattered near infrared light is collected by the plurality of light detectors 16. In another exemplary embodiment, a light detector 16 is disposed near the peripheral edge of the substrate 18 instead of near the center of the substrate 18, and a plurality of near infrared sources 14 are disposed at various locations on the substrate 18.

Figure 3:
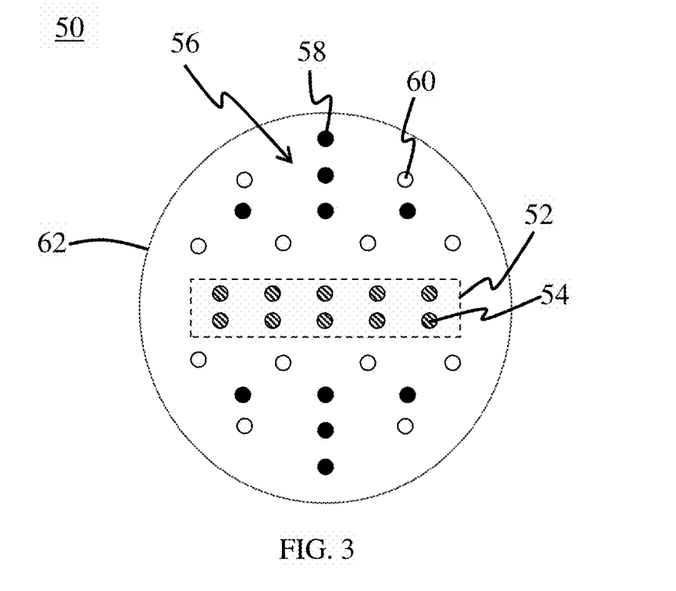
FIG. 3 shows a front view of a primary probe according to an exemplary embodiment.
Figure 4:
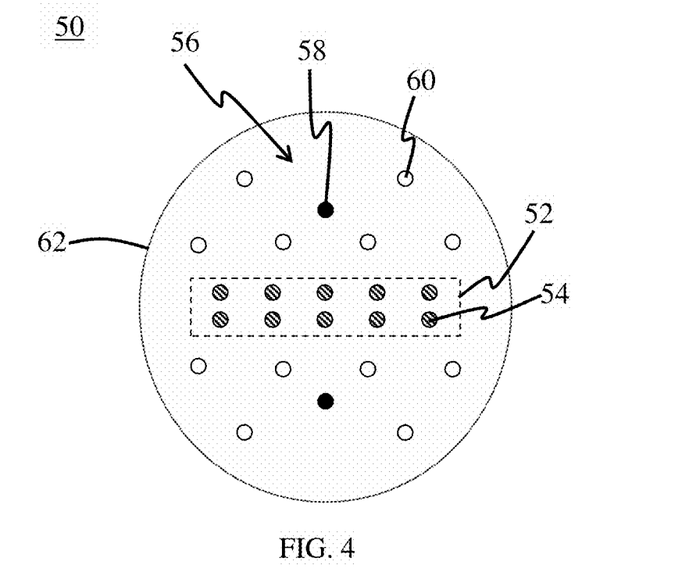
FIG. 4 shows a front view of a primary probe according to an exemplary embodiment.

With reference to FIGS. 3 and 4, the primary probe 50 includes a transducer array 52 and a near infrared array 56 disposed in a substrate 62. The transducer array 52 has a plurality of ultrasound transducer array 54 and is disposed between near infrared arrays 56, which include a near infrared source 58 and light detector 60. Such a primary probe 50 is described in U.S. Pat. Nos. 6,264,610 and 8,070,682, the disclosures of each of which are incorporated by reference herein in their entirety. For convenience, the ultrasound transducers 54 are disposed between at least two near infrared sources 58. The geometric pattern of the near infrared source 58 and light detector 60 in the near infrared array 56 can be many different patterns that include various numbers of near infrared sources 58 and light detectors 60. The ultrasound transducer array 52 with its ultrasound transducers 54 can be connected to a commercially available ultrasound system that provides ultrasound frequencies to the ultrasound transducers 54 and that receives ultrasound echo frequencies from the ultrasound transducers 54. In another embodiment, the ultrasound array 52 with its ultrasound transducers 54 can be readily available from a commercially available ultrasound system.

As will be appreciated, the auxiliary probe 10 and the primary probe 50 both include a near infrared source and light detector. However, the primary probe 50 additionally includes the ultrasound transducer array 52 disposed centrally among the near infrared source 58 and light detector 60 such that a pair of a near infrared source 58 and light detector 60 is separated by at least a width of the transducer array 52, i.e., in a source-detector pair, the near infrared source 58 is on an opposite side of the ultrasound transducer array 52 with respect to the light detector 60. Since the auxiliary probe 10 has a near infrared source 14 and light detector 16 in closer proximity over the active area of the auxiliary probe 10 as compared to the primary probe 50, the auxiliary probe 10 can be used to accurately determine optical parameters of normal tissue to be used as a reference or background value while the primary probe 50 can acquire scattered light and ultrasound echo frequencies for imaging an inclusion in an abnormal tissue, with background corrections of tissue functional properties using the background values derived from the auxiliary probe 10 data.

The near infrared sources 14, 58 can produce or transmit the near infrared radiation. The near infrared radiation can have a wavelength from 600 nanometers (nm) to 2000 nm, specifically 700 nm to 1000 nm, and more specifically 700 nm to 900 nm. In an embodiment, the near infrared wavelength has a wavelength chromaticity of $\Delta\lambda/\lambda$ from 0.1% to 40%, specifically from 1% to 30%, and more specifically from 5% to 25%, where $\lambda$ is a wavelength in nanometers, and $\Delta\lambda$ is determined at the full width half maximum of the emission band of the near infrared radiation. More than one near infrared wavelength can be used such that in the near infrared arrays 12 and 56 (FIGS. 1 and 2) individual light from the first and second near infrared light sources 58, 14 independently can transfer different near infrared wavelengths to different portions of the first and second tissues. In other words, in the near infrared array 12, different near infrared light sources 14 can provide different near infrared wavelengths to the second tissue. Further, the number of different wavelengths delivered by the near infrared sources 14, 58 can be from 1 to 20, specifically 1 to 10, and more specifically from 1 to 5. The near infrared wavelength can be selected based on a particular chromophore that is selected to be interrogated by the near infrared light. Exemplary chromophores include those found in or added to biological tissue such as oxygenated hemoglobin (oxyHb), deoxygenated (deoxyHb), molecular probes, cellular probes, markers, antibodies, contrast agents, carbohydrates (e.g., glucose), lipids, water, cytochromes, and the like. The peak wavelength of the near infrared wavelength from the first 58 or second 14 near infrared source therefore can be tuned or selected to be resonant with the peak in the absorption band of such a chromophore. In an embodiment, a plurality of near infrared wavelengths is used from the near infrared source 14, 58 and corresponds to a peak in the absorption band of deoxyHb and oxyHb. In some embodiments, the near infrared wavelengths have an emission peak wavelength of, e.g., 740 nm, 780 nm, 808 nm, 830 nm, and the like.

In an embodiment, the near infrared sources 14, 58 are independently an optical fiber, infrared emitter, and the like. Consequently, the near infrared radiation at the auxiliary probe 10 or primary probe 50 can be produced at a location external to the auxiliary probe 10 or primary probe 50. Any source that produces near infrared radiation can be used as long as the photon fluence is sufficient to make a scattered signal that is great enough to be detected and statistically significant for determination of optical parameters of the second tissue and functional parameters of the first tissue. As previously indicated, the near infrared radiation from the first or second near infrared source 14, 58 is diffusive near infrared radiation with, e.g., an up to 40% chromaticity such that a large amount of biological chromophores will be excited by the diffusive near infrared radiation.

The near infrared sources can be various implements such as a near infrared emitter or an optical fiber, which can be optically coupled to the near infrared emitter. In the latter case, the infrared emitter can be external to the primary or auxiliary probe 50, 10. The near infrared emitter can be a light emitting diode, solid state laser, lamp, filament, flash lamp, dye, or a combination comprising at least one of the foregoing. In an embodiment, a light emitting diode is disposed in the primary or auxiliary probe 50, 10. In a further embodiment, the near infrared source is an optical fiber, which is coupled to a laser diode disposed, e.g., in an optical tomography device. Such near infrared emitters are commercially available, e.g., a halogen gas lamp available from Avantes, a near infrared lamp available from Helioworks, Inc., a near infrared dye available from American Dye Source, or a laser diode available from Thor Labs.

The optical fibers used as the near infrared source to transmit near infrared radiation from the near infrared emitter can be various sizes, i.e., have various diameters, including a diameter from 25 micrometers (μm) to 300 μm, specifically 50 μm to 250 μm, and more specifically 50 μm to 200 μm. The optical fibers can be made of an optical material that transmits, e.g., near infrared light with high efficiency.

The near infrared emitter can produce the near infrared wavelength as a continuous wave, modulated wave, pulsed light, and the like, without limitation to time resolved or time domain properties. The light can be modulated either within the near infrared emitter driven by, e.g., a function generator or by an external mechanical element such as a light chopper, including a rotary wheel or tuning fork, to produce a pulsed near infrared wavelength. The pulse length of the light and duty cycle can be from any length and duty factor effective to scatter within the biological tissue or for absorption by a chromophore in the tissue. The pulse length can be, e.g., greater than 100 nanosecond (ns), specifically greater than 500 ns, and more specifically greater than 1000 ns. The duty cycle can be 1% to 100%, specifically 5% to 100%, and more specifically 50% to 100%.

The light detector can detect near infrared wavelengths such as those scattered by biological tissue. Exemplary light detectors include a photodiode (e.g., an avalanche photodiode), photomultiplier, carrier multiplication device, semiconductor detector (e.g., silicon detector, germanium-silicone detector), bolometer, or a combination comprising at least one of the foregoing. A thermostatic or cooling system can be used with the light detector to achieve a stable gain curve. The light detector can include an optical fiber disposed in the substrate of the primary or auxiliary probe to collect scattered photons or emitted photons from a chromophore excited by the near infrared wavelength from a near infrared source of the primary or auxiliary probe. The optical fiber transmits such detected light to the photosensitive device (e.g., the photodiode, photomultiplier, carrier multiplication device, semiconductor detector, bolometer, and the like).

The near infrared sources 15, 58, light detectors 16, 60, and ultrasound transducers 54 are disposed in a substrate 18, 68, which is a material strong enough to contain these elements. The material can be selected to be compatible with biological tissue. Exemplary materials include plastic, ceramic, glass, metal, or a combination thereof. In a particular embodiment, the substrate 18, 68 is a metal such as stainless steel, nickel, aluminum, and the like; a resin such as silicone, acrylonitrile-butadiene-styrene, polyurethane, polyimide, and the like; or a combination thereof. In certain embodiments, the substrate is flexible such that the substrate can conform to the contour and shape of body structure, e.g., a breast. The substrate can be any shape (e.g., round or rectangular) and size. In some embodiment, the auxiliary probe is smaller than the primary probe.

Figure 5:
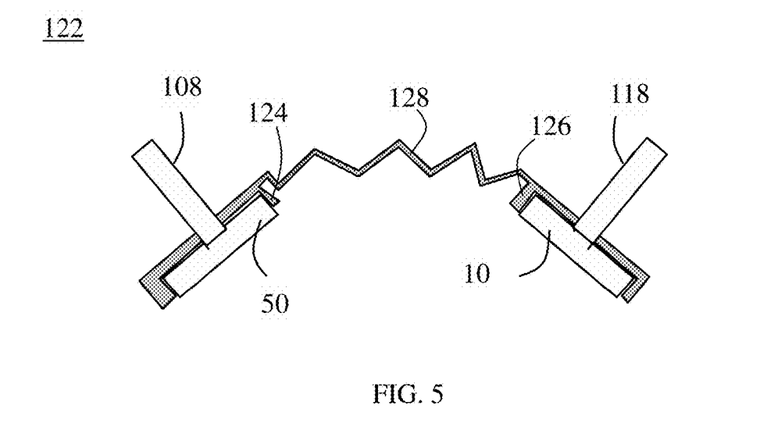
FIG. 5 shows a cross section of primary and auxiliary probes in a probe housing.

According to an embodiment, as shown in FIG. 5, an imaging device 122 includes a container 124, 126 in which to dispose the primary probe 50 and auxiliary probe 10. The imaging device 122 can include a member 128 that couples the containers 124, 126. The member 128 can be made of a flexible or elastic material (e.g., a silicone) so that the primary 50 and auxiliary 10 probes are mobile with respect to one another. Further, this construction allows the primary probe 10 and auxiliary probe 50 to conform to body structures that have different, same, or complimentary shapes. In some embodiments a line 108, 118 (e.g., a communication line, signal line, optical fiber, and the like) is connected to the optical and ultrasound elements of the primary and auxiliary probes 50, 10. The containers are designed to accommodate or support the line 108, 118.

Figure 6:
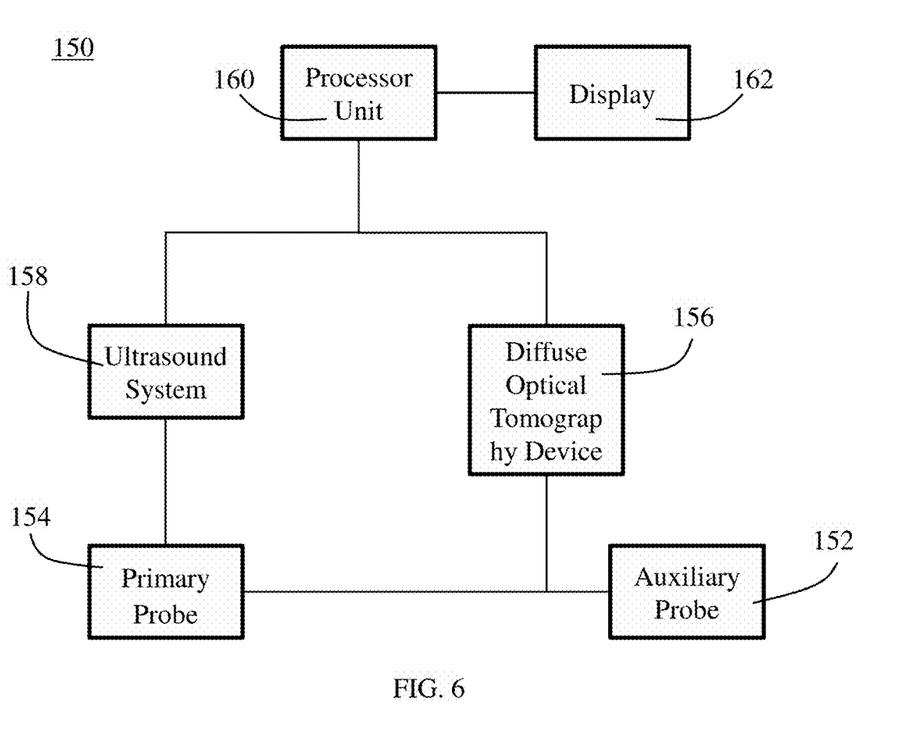
FIG. 6 shows a diagram of interconnections among an imaging system.

As shown in FIG. 6, a system 150 for imaging includes a primary probe 154 to irradiate a first tissue, an auxiliary probe 152 to irradiate a second tissue, a diffuse optical tomography device 156 connected to the auxiliary probe 152 and the primary probe 154, an ultrasound device 158 connected to the primary probe 154, and a processor unit 160 operatively connected to the optical tomography device 156 or the ultrasound system 158. A display device 162 is connected to the processor unit 162 to display an image of a tissue, e.g., an inclusion in the first tissue. The diffusive optical tomography (DOT) device 156 contains a near infrared emitter coupled to the primary probe 154 and auxiliary probe 152 through, e.g., an optical fiber, a detector such as a photomultiplier tube coupled through optical fiber to light detectors disposed in the primary probe 154 and auxiliary probe 152, and electronics to drive the near infrared emitter and light detectors as well as electronics to send acquired data signals to the processor unit 160. The acquired data signals correspond to scattered or emitted near infrared light from the first or second tissue. The processor unit 160 receives data from the ultrasound system 158 and DOT device to construct images of the first tissue, which can be printed or observed on the display 162. Details of the operation of the ultrasound system 158, DOT device 156, and processor unit 160 are described in U.S. Pat. Nos. 6,264,610 and 8,070,682, the disclosures of each of which are incorporated by reference herein in their entirety.

The auxiliary probe 152 is configured to irradiate the second tissue with an infrared wavelength from the DOT device 156. The second tissue scatters the near infrared light, and optical fibers of the auxiliary probe 152 collect the scattered near infrared photons and transmit them to the detector housed in the DOT device 156. The detector, e.g., a photomultiplier tube detects the transmitted photons and transforms the scattered photons into an electrical signal (e.g., voltage or current) that is amplified by a post-detector amplifier. The amplified signal is transmitted from the DOT device 156 to the processor unit 160. Similarly, the primary probe 154 receives a near infrared wavelength from the DOT device 156, which is transmitted to the first tissue by an optical fiber in the primary probe 154. Optical fibers collect scattered photons from the first tissue, which are transmitted to the DOT device 156 from the primary probe 154. In addition, the ultrasound transducer of the primary probe 154 receives ultrasound frequencies from the ultrasound system 158 and transmits them to the first tissue. Ultrasound echo frequencies are then acquired from the first tissue by the primary probe 154 and transmitted from the ultrasound transducers therein to the ultrasound system 158. The processor unit 160 subsequently receives data from the ultrasound system 158 and the DOT device 156 respectively corresponding to the acquired ultrasound echo frequencies and scattered near infrared photons.

In an embodiment, the processor unit 160 is configured to receive a first detected near infrared wavelength acquired by the primary probe 154, ultrasound echo frequency acquired by the primary probe 154, and second detected near infrared wavelength acquired by the auxiliary probe 152. Further, the processor unit 160 determines a tissue property of an inclusion disposed in the first tissue from the first and second detected near infrared wavelengths. Exemplary tissue properties of the inclusion include angiogenesis, hypoxia, optical absorption, oxygenated hemoglobin concentration, deoxygenated hemoglobin concentration, total hemoglobin concentration, oxygen saturation, or a combination comprising at least one of the foregoing properties. The tissue property of the inclusion is determined by the processor unit 160 from an optical property of the second tissue. The optical property of the second tissue is derived from the detected second near infrared wavelength acquired by the auxiliary probe 152 and comprises an optical absorption coefficient, reduced scattering coefficient, or a combination comprising at least one of the foregoing optical properties. Details of the algorithms used to derive tissue properties and optical properties from the acquired first and second near infrared wavelengths, guided by ultrasound echo frequencies acquired by the ultrasound transducer, are described for example in U.S. Pat. Nos. 6,264,610 and 8,070,682.

Figure 7:
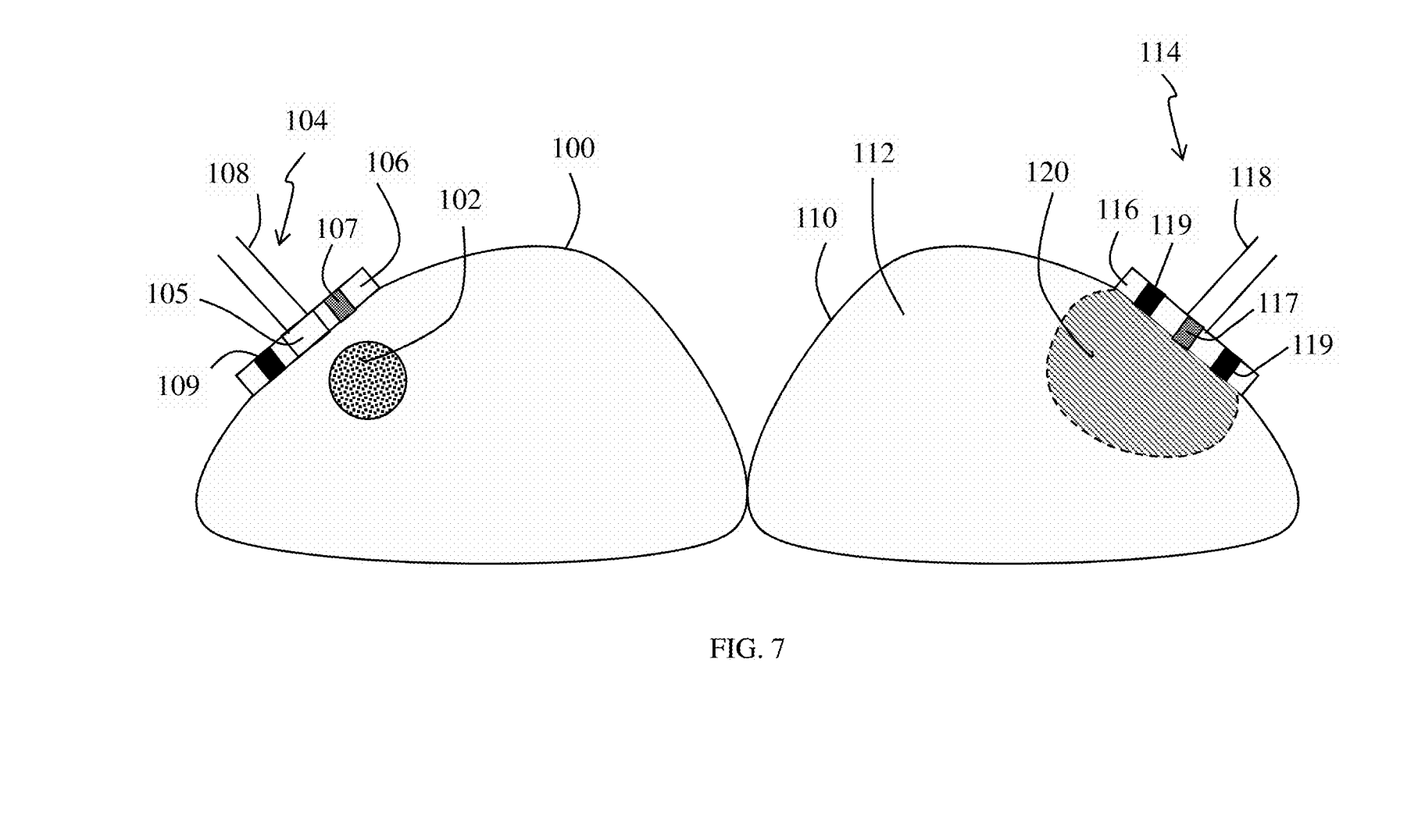
FIG. 7 shows a cross-section of an imaging system in contact with breast tissue.

According to an embodiment, the imaging system 122 can be used to produce morphological and functional maps of biological tissue, including breast tissue. As shown in FIG. 7, a primary probe 104 is disposed on a breast 100 having an inclusion 102. The primary probe 104 includes an ultrasound transducer 105, first near infrared source 107, and first light detector 109 disposed in a substrate 106. Lines 108 couple the primary probe 104 to the DOT device 156 and ultrasound system 158. An auxiliary probe 114 is disposed on a contralateral breast 110 having normal breast tissue 112. The auxiliary probe 114 includes a second near infrared source 117 and second light detector 119 disposed in a substrate 116 and also includes lines 118 that couple the auxiliary probe 114 to the DOT device 156. The inclusion 102 of the breast 100 is irradiated by near infrared radiation and ultrasound frequencies respectively transmitted by the first near infrared source 107 and ultrasound transducer 105 of the primary probe 104. The second near infrared source 117 of the auxiliary probe 116 irradiates normal tissue 112 of the contralateral breast 110 in the region 120 corresponding to a position of the inclusion 102 in the breast 100. Then, normal tissue 112 in the region 120 of the contralateral breast 110 absorbs and scatters the second near infrared wavelength. The scattered light is detected by the second light detector 119, which transmits the scattered light through optical fibers to be detected by a detector in the DOT device 156. The DOT device 156 transmits signals to the processor unit 160, which uses the signals from the detected light of the auxiliary probe 114 in combination with data signals from the primary probe 104 to form real-time images based on geometry of the constituents of the probes 104, 114 and using diffusion equations since the near infrared photons are diffusively scattered in the breast tissue. In an alternative embodiment, the auxiliary probe 114 can be disposed on the breast 100, and the primary probe 104 can be disposed on the contralateral breast 110. Here, the contralateral breast 110 may have some tissue that has a potential abnormality but which is not quite visible by ultrasound. Moreover, the breast 100 does not have an inclusion 102 that is detectable by near infrared irradiation, i.e., any inclusion 102 is not detected within the resolution of near infrared techniques and thus could appear to be normal tissue when subjected to near infrared radiation. In this manner, the contralateral breast 110 can be subjected to both ultrasound frequencies and near infrared radiation from the primary probe 104 while the auxiliary probe 114 provides background optical properties from the breast 100. As a result, the contralateral breast 110 can be screened and imaged for inclusions including tumor growth using the auxiliary probe 104.

For body tissue that is symmetric in location such as the left and right breasts, tissue parameters are also symmetric. Thus, tissue parameters determined from the contralateral breast 110 is used as an estimate of the background (reference) values for construction of images for the inclusion 102 of the breast 100. The acquired scattered photon signal from the normal tissue 112 of the contralateral breast 110 is used by the processor unit 150 as fitting parameters in an optimization algorithm to determine optical parameters of normal tissue 112 such as optical absorption coefficients and reduced scattering coefficients. The processor unit 160 then uses the optical parameters of the normal tissue 112 to determine a perturbation of the breast tissue 100 due to the inclusion 102 by an iterative algorithm. The difference derived by the scattered photons in the breast 100 and the contralateral breast 110 is related to any inclusion 120 sampled by the primary probe 106.

The resulting image data derived from the algorithm implemented by the processor provides an image of the inclusion 102 with vascularization derived from the near infrared data from the primary probe 104 and auxiliary probe 114 and anatomical features derived from the ultrasound transducer 105 of the primary probe 104. The near infrared signals give functional information such as vasculature of the inclusion 102 that can be related to near infrared light absorption, which is an optical signature of chromophores, e.g., hemoglobin in its deoxygenated and oxygenated states. Consequently, the near infrared source provides functional parameters, and the ultrasound transducer provides morphological data in the construction of the images of an inclusion disposed in tissue.

Thus, in an embodiment, a process for imaging includes disposing a primary probe on a first tissue, disposing an auxiliary probe on a second tissue, irradiating the first tissue with a first near infrared wavelength and an ultrasound frequency from the primary probe, and irradiating the second tissue with a second near infrared wavelength from the auxiliary probe to produce an image of the first tissue. The primary probe includes a first near infrared source, first light detector, and ultrasound transducer, and the auxiliary probe includes a second near infrared source and second light detector. The process also includes using the second light detector to detect a second detected wavelength from the second tissue in response to irradiating the second tissue with the second near infrared wavelength. The second tissue can be, e.g., normal breast tissue, and the first tissue can include an abnormality such as an inclusion. An optical property of the second tissue is determined from the second detected wavelength. The inclusion disposed in the first tissue is irradiated with the first near infrared wavelength and ultrasound frequency. Then, the ultrasound transducer acquires an ultrasound echo frequency from the first tissue in response to irradiating the first tissue with the ultrasound frequency. The first light detector acquires a first detected wavelength from the first tissue in response to irradiating the first tissue with the first near infrared wavelength. Thereafter, the ultrasound echo frequency is processed, e.g., by a processor unit, to produce morphology data of the inclusion, and the optical property of the second tissue is used to produce functional data of the inclusion. The functional data includes angiogenesis, hypoxia, optical absorption, oxygenated hemoglobin concentration, deoxygenated hemoglobin concentration, total hemoglobin concentration, oxygen saturation, or a combination comprising at least one of the foregoing properties. The morphology and functional data are then displayed as an image of the inclusion.

The imaging system herein has several advantages and benefits. While the primary probe is disposed on abnormal tissue, the auxiliary probe is disposed on contralateral tissue to determine parameters of the normal tissue that are used to create functional maps, e.g., vascularization and chromophore concentration, which can be overlaid or compared with morphological images from ultrasound images. Thus, the imaging system allows for real time imaging of abnormal tissue.

In addition, when a single dual probe (a primary probe) having an ultrasound transducer array and near infrared array is used to image abnormal tissue, e.g., a breast lesion, that is close to the ultrasound transducer rather than deep in the tissue, estimated bulk tissue parameters that are used as the background values for that tissue are inaccurate due to the geometric configuration of the ultrasound transducer relative to the near infrared array. Here, the central portion of the dual probe is missing near infrared excitation sources for illumination of the tissue because of the central position of the ultrasound transducer. With the use of the primary and auxiliary probe herein, the auxiliary probe alleviates the problems associated with bulk tissue parameter determination for use in background correction since the auxiliary probe has a near infrared source or detector centrally disposed in the auxiliary probe instead of having an ultrasound transducer array interposed between near infrared source-detector pairs that are used for bulk parameter determination. The contralateral normal breast tissue parameters, i.e., bulk parameters, are therefore more accurately determined using the auxiliary probe. The use of the primary and auxiliary probes together also allows accurate determination of bulk tissue parameters even when an interfering structure, such as the chest wall, is proximal to the probes, which would ordinarily limit the use of a single primary probe.

The imaging system comprising the primary and auxiliary probes is further illustrated by the following example, which is non-limiting.

EXAMPLES

Example 1

Bulk Tissue Parameter Estimation. To obtain bulk tissue parameters, e.g., the optical absorption coefficients or reduced scattering coefficients, scattering data acquired from near infrared source-light detector pairs are used. The photons detected from scattering of the near infrared light by tissue include amplitude and phase data, which is provided to a fitting algorithm to determine the bulk tissue parameters.

Figure 8:
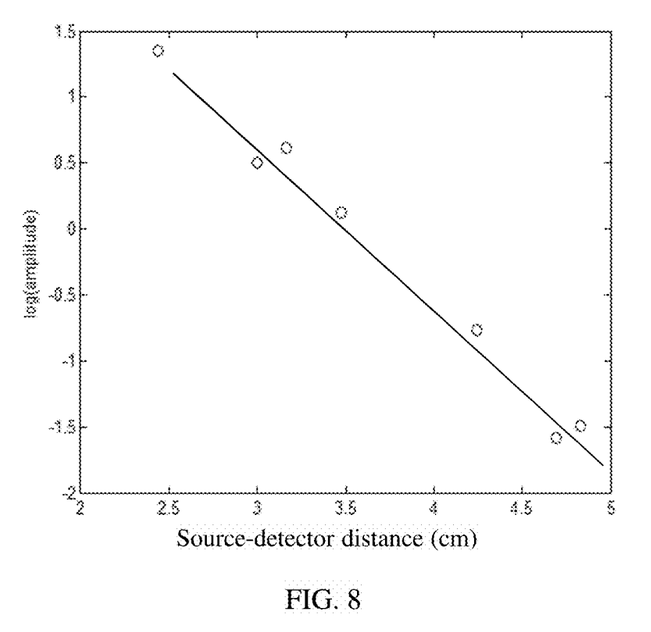
FIG. 8 shows a graph of log(amplitude) versus source-detector distance for an auxiliary probe disposed on normal breast tissue.
Figure 9:
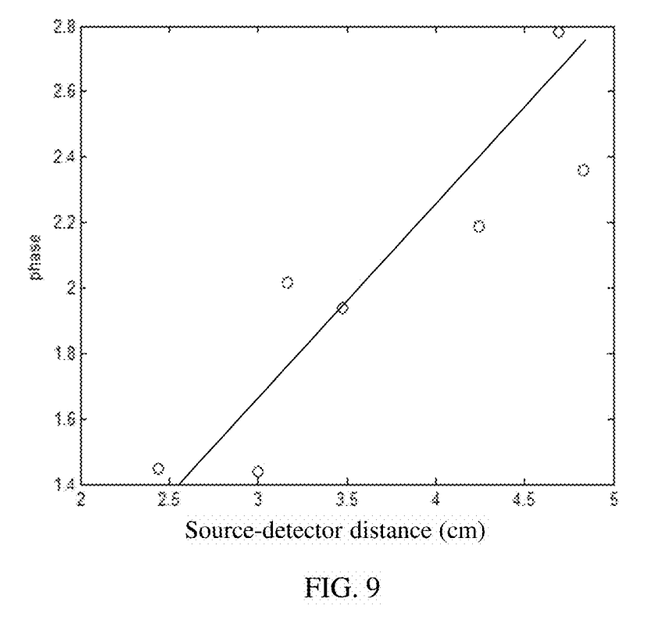
FIG. 9 shows a graph of phase versus source-detector distance corresponding to the amplitude data shown in FIG. 8.

For two different probes, breast tissue of a 54-year old woman was irradiated with near infrared radiation, and scattered light was detected. FIGS. 8 and 9 respectively show the amplitude and phase plots as a function of near infrared source-detector distance obtained using an auxiliary probe having a single near infrared source centrally disposed among a plurality of light detectors. The amplitude (log scale) (FIG. 8) decreases linearly with source-detector distance, and the phase (FIG. 9) increases linearly with source-detector distance. These results are accurately predicted by light diffusion theory. Thus, the auxiliary probe approximates an ideal optical tissue probe.

Figure 10:
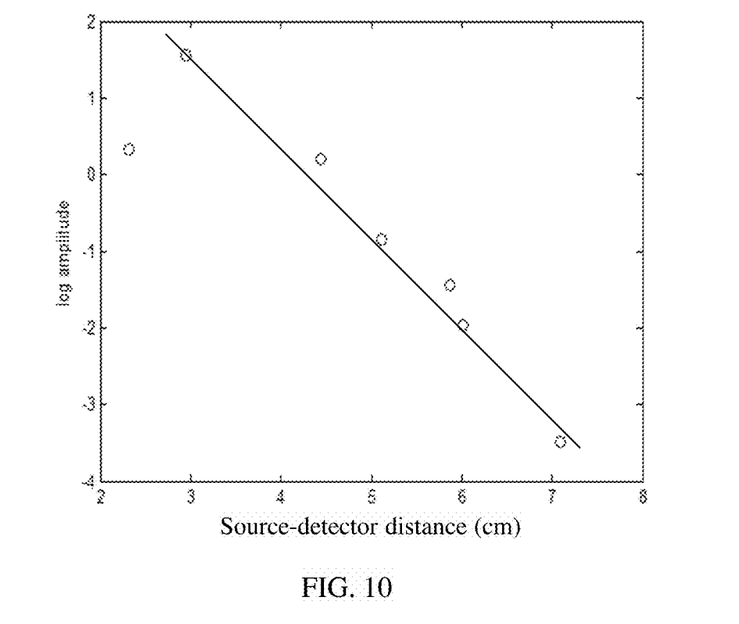
FIG. 10 shows a graph of log(amplitude) versus source-detector distance for a primary probe using normal breast tissue.
Figure 11:
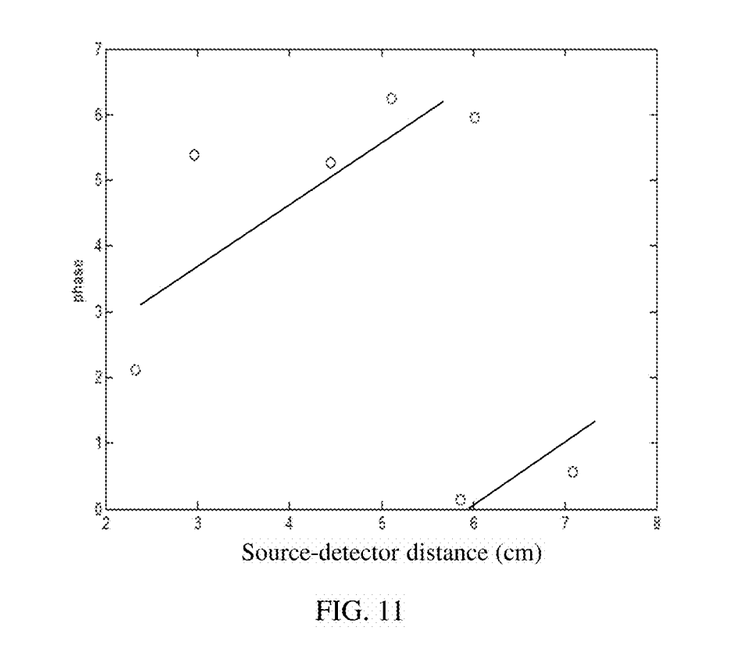
FIG. 11 shows a graph of phase versus source-detector distance corresponding to the amplitude data shown in FIG. 10.

However, as shown in FIGS. 10 and 11, when optical data were obtained from the same woman using a primary probe with an ultrasound transducer centrally disposed among near infrared arrays (having near infrared sources and light detectors), the amplitude (FIG. 10) exhibits a more drastic decrease than the detected amplitude for the auxiliary probe (FIG. 8). Moreover, the phase (FIG. 11) wraps around $2\pi$ over the larger source-detector distance of the primary probe, and estimated optical properties derived therefrom were incorrect. To unwrap the phase that causes spurious optical properties, a manual operation is often needed. This problem becomes more pronounced as the size of the breast decreases or as the breast tissue becomes denser.

Example 2

Figure 12:
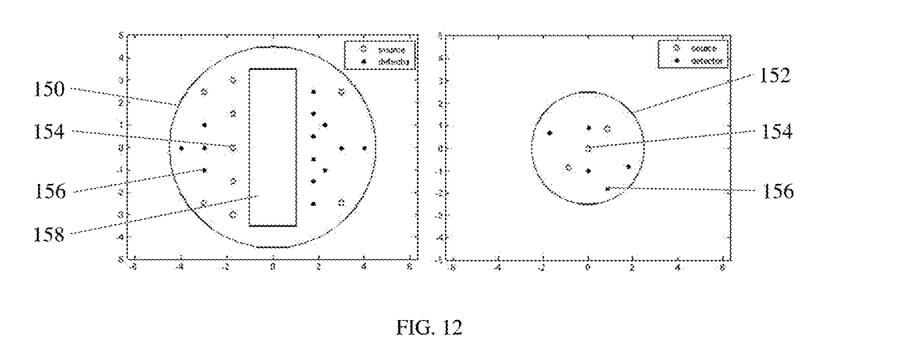
FIG. 12 shows a cross section of a primary probe and an auxiliary probe.

Dual Probe Investigation. Imaging experiments and simulations were conducted for a dual probe imaging system that was configured with a primary probe 150 and an auxiliary probe 152 as shown in FIG. 12. The primary probe 150 and the auxiliary probe 152 had a light source 154 and a light detector 156. An ultrasound transducer 158 was provided in the primary probe 150, which had a 10 cm diameter. The auxiliary probe 152 had a relatively short distance between the light source 154 and the light detector 156. Data from the auxiliary probe 152 rendered an accurate estimation of background optical properties.

Figure 13:
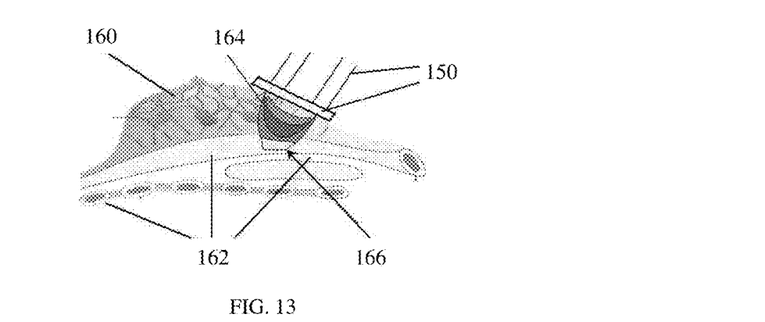
FIG. 13 shows a side perspective of an imaging probe disposed on breast tissue.

It is contemplated that this dual probe configuration is especially useful for imaging human breast with a small amount of breast tissue, e.g., a breast tissue thickness of less than 2 cm, and more specifically less than 1.5 cm. For this investigation, the imaging media was modeled as a two-layer medium with the breast tissue modeled as a first layer 160 and the chest wall muscle as a second layer 162, as depicted in FIG. 13. The primary probe 150 emitted diffused light having a banana-shaped optical path 164 through the first layer 160 and second layer 162. A portion of the optical path was perturbed and had a distorted shape 166. It is contemplated that the effective optical path length depends on the first layer tissue optical absorption and scattering coefficients as well as the depth of the first layer relative to the probe.

Accuracy of the background tissue optical property calibration was determined for the auxiliary probe 152 shown in FIG. 12 using a two-layer tissue model. The two-layer tissue model was constructed from a liquid phantom as the first layer 160 and a solid tissue-mimicking phantom as the second layer 162. The liquid phantom layer varied in thickness to model breast tissue having multiple thicknesses, and three liquid phantoms were used to obtain optical properties of breast tissues (first layer 160). The solid phantom had optical properties of a muscle layer (second layer 162).

Figure 14:
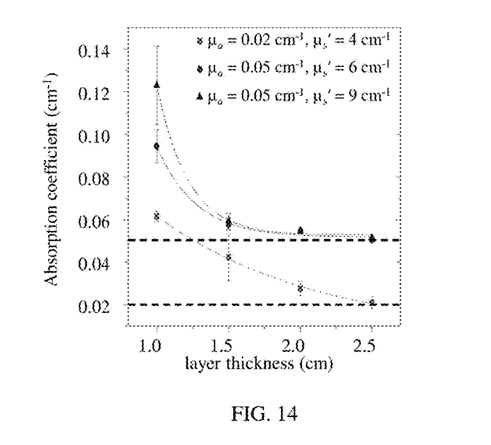
FIG. 14 shows a graph of absorption coefficient of a first layer versus first layer thickness.
Figure 15:
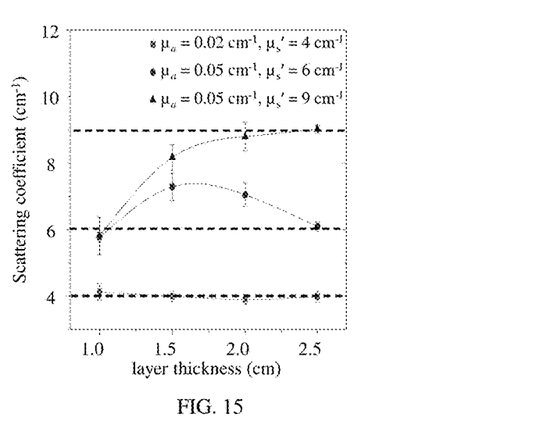
FIG. 15 shows a graph of reduced scattering coefficient of a first layer versus first layer thickness.

Calibration results for optical parameters of the two-layer tissue model are shown in FIGS. 14 and 15. The calibrated absorption coefficient versus layer thickness is shown in FIG. 14, and the calibrated reduced scattering coefficient versus layer thickness is shown in FIG. 15. Four layer thicknesses (1.0 cm, 1.5 cm, 2.0 cm, and 2.5 cm) were studied, and the dashed lines in FIGS. 14 and 15 are the true values for first layer 160 optical properties. Calibration results were most accurate when the first layer thickness was about 1.5 cm or greater, which corresponds to in vivo imaging conditions often encountered.

Figure 16:
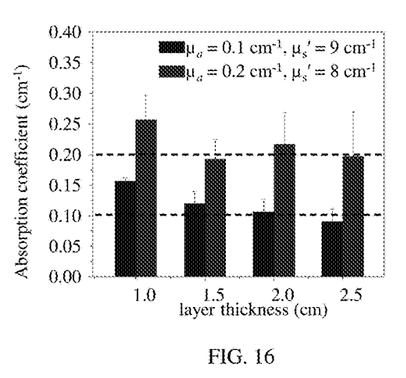
FIG. 16 shows a bar chart of absorption coefficient of a second layer versus first layer thickness.
Figure 17:
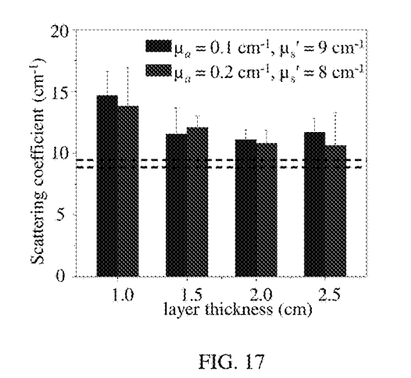
FIG. 17 shows a bar chart of reduced scattering coefficient of a second layer versus first layer thickness.

The first layer optical properties obtained from imaging data of the auxiliary probe was used to estimate the second layer background optical properties. The data acquired from the primary probe was fit using the two-layer tissue model. As shown in FIGS. 16 and 17, the second layer phantom optical properties were accurately recovered for first layer tissue thicknesses from 1 cm to 2.5 cm. FIG. 16 shows the second layer absorption coefficient versus first layer thickness, and FIG. 17 shows the second layer reduced scattering coefficient versus first layer thickness. The error bars indicate estimation accuracy based on pooled data for a given thickness, and the dashed lines in FIGS. 16 and 17 correspond to the true value of the fitted properties. Minimum and maximum values of the horizontal dashed lines represent the range of true optical values for the first layer tissue thicknesses. Such results are not obtained when a single imaging probe is used for imaging media containing multiple tissue layers having different optical properties.

Example 3

Figure 18:
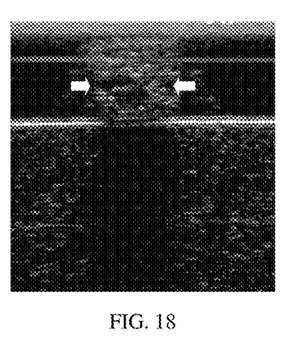
FIG. 18 shows a co-registered image of a target.
Figure 19:
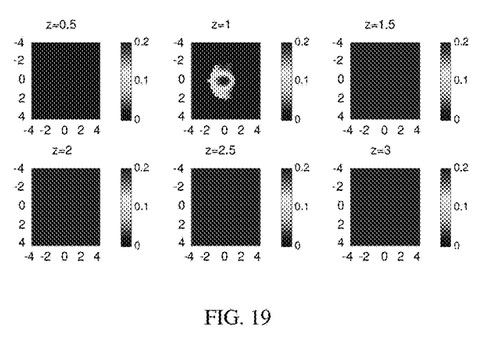
FIG. 19 shows absorption maps for the target shown in FIG. 18.
Figure 20:
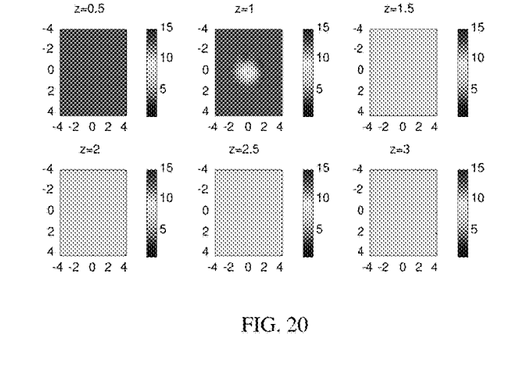
FIG. 20 shows reduced scattering maps for the target shown in FIG. 18.

Optical Property Mapping. Co-registered near-infrared/ ultrasound image data of a phantom target were acquired using a dual imaging probe having an ultrasound transducer centrally disposed in the primary probe as described in Example 2. The phantom target is indicated by the two arrows in the co-registered image shown in FIG. 18. The phantom target was spherical with a 1 cm diameter and was located in a first layer liquid medium on top of a second layer solid phantom with respect to the primary probe. Reconstructed absorption maps for the target are shown in FIGS. 19 and 20. Particularly, a reconstructed absorption map is shown in FIG. 19, and the reduced scattering map is shown in FIG. 20. The accurate reconstruction of optical properties for the target was achieved with an estimation of the two-layer background optical properties as described in Example 2. The target had an absorption coefficient $\mu_a$ of 0.18 cm$^{-1}$ and a reduced scattering coefficient $\mu_s'$ of 11.0 cm$^{-1}$. The first layer medium thickness was 1.5 cm with background optical properties of $\mu_a=0.02$ cm$^{-1}$ and $\mu_s'=4.0$ cm$^{-1}$. The second layer phantom background optical properties were $\mu_a=0.2$ cm$^{-1}$ and $\mu_s'=8.0$ cm$^{-1}$. Beneficially, the target absorption and reduced scattering coefficients respectively were recovered to within 113% and 94% of the true value. These results were unattainable from a single imaging probe configuration.

The singular forms "a," "an," and "the" include plural referents unless the context clearly dictates otherwise. "Or" means "and/or."

Various numerical ranges are disclosed in this patent application. Because these ranges are continuous, they include every value between the minimum and maximum values. The endpoints of all ranges reciting the same characteristic or component are independently combinable and inclusive of the recited endpoint.

All references are incorporated herein by reference.

While the invention has been described with reference to various embodiments, it will be understood by those skilled in the art that various changes can be made and equivalents can be substituted for elements thereof without departing from the scope of the invention. In addition, many modifications can be made to adapt a particular situation or material to the teachings of the invention without departing from the essential scope thereof. Therefore, it is intended that the invention not be limited to any particular embodiment disclosed for carrying out this invention, but that the invention will include all embodiments falling within the scope of the appended claims.

What is claimed is:

1. An imaging system comprising:
   a primary probe comprising:
      a substrate;
      an ultrasound transducer disposed in the substrate to irradiate a first tissue with an ultrasound frequency;
      a first near infrared source disposed in the substrate to irradiate the first tissue with a first near infrared wavelength; and
      a first light detector disposed in the substrate to detect a first detected wavelength from the first tissue; and
   an auxiliary probe comprising:
      a second near infrared source configured to irradiate a second tissue with a second near infrared wavelength; and
      a second light detector configured to detect a second detected wavelength from the second tissue,
   wherein the second detected wavelength is used to determine an optical property of the second tissue, the optical property of the second tissue is used to determine a tissue property of the first tissue based on the first detected wavelength, and
   the tissue property is a property of an inclusion, lesion, or tumor and comprises angiogenesis, hypoxia, blood oxygen saturation, oxygenated hemoglobin concentration, deoxygenated hemoglobin concentration, total hemoglobin concentration, or a combination comprising at least one of the foregoing properties.

2. The imaging system of claim 1, wherein the second near infrared source is interposed between at least two second light detectors.

3. The imaging system of claim 1, wherein the second near infrared source is disposed between a majority of all of the second light detectors.

4. The imaging system of claim 1, wherein the second light detector is interposed between at least two second near infrared sources.

5. The imaging system of claim 1, wherein the second light detector is centrally disposed among all second near infrared sources.

6. The imaging system of claim 1, wherein the ultrasound transducer of the primary probe is interposed between at least two first near infrared sources.

7. The imaging system of claim 1, wherein the first or second near infrared source comprises an optical fiber connected to an optical tomography device, which comprises a near infrared emitter to emit the first or second near infrared wavelength.

8. The imaging system of claim 7, wherein the near infrared emitter is a light emitting diode, solid state laser, lamp, dye, or a combination comprising at least one of the foregoing.

9. The imaging system of claim 7, wherein the near infrared emitter emits a wavelength from 600 nm to 1500 nm.

10. The imaging system of claim 1, wherein the second near infrared wavelength comprises at least two near infrared wavelengths.

11. The imaging system of claim 1, further comprising a housing, wherein the primary probe and the auxiliary probe are disposed in the housing.

12. A system for imaging comprising:
   a primary probe to irradiate a first tissue;
   an auxiliary probe to irradiate a second tissue;
   an optical tomography device connected to the auxiliary probe and the primary probe;
   an ultrasound device connected to the primary probe; and
   a processor unit connected to the optical tomography device, the processor unit being configured to background-correct data of the first tissue collected by the primary probe using data of the second tissue collected by the auxiliary probe in real time.

13. The system of claim 12, wherein
   the primary probe comprises an ultrasound transducer and a first near infrared source;
   the auxiliary probe comprises a first near infrared source;
   the auxiliary probe is configured to be simultaneously used with the primary probe; and
   the processor unit is configured:
      to receive a first detected near infrared wavelength acquired by the primary probe, an ultrasound echo frequency acquired by the primary probe, and a second detected near infrared wavelength acquired by the auxiliary probe; and
      to determine a tissue property of an inclusion disposed in the first tissue from the first and second detected near infrared wavelengths.

14. The system of claim 13, wherein the tissue property of the inclusion comprises angiogenesis, hypoxia, optical absorption, oxygenated hemoglobin concentration, deoxygenated hemoglobin concentration, total hemoglobin concentration, oxygen saturation, or a combination comprising at least one of the foregoing properties.

15. The system of claim 13, wherein the tissue property of the inclusion is determined by the processor unit from an optical property of the second tissue which is derived from the detected second near infrared wavelength acquired by the auxiliary probe.

16. The system of claim 15, wherein the optical property comprises an optical absorption coefficient, reduced scattering coefficient, or a combination comprising at least one of the foregoing optical properties.

17. A process for imaging, the process comprising:
disposing a primary probe on a first tissue, the primary probe comprising a first near infrared source, first light detector, and ultrasound transducer;
disposing an auxiliary probe on a second tissue, the auxiliary probe comprising a second near infrared source and second light detector;
irradiating the first tissue with a first near infrared wavelength and an ultrasound frequency from the primary probe;
irradiating the second tissue with a second near infrared wavelength from the auxiliary probe to produce an image of the first tissue; and
in real time, background-correcting data of the first tissue collected by the primary probe using data of the second tissue collected by the auxiliary probe.

18. The process of claim 17, further comprising detecting, with the second light detector, a second detected wavelength from the second tissue in response to the irradiating the second tissue with the second near infrared wavelength, wherein the second tissue is normal breast tissue; and
the process comprises simultaneously using the primary probe and the auxiliary probe.

19. The process of claim 18, further comprising determining an optical property of the second tissue from the second detected wavelength.

20. The process of claim 17, wherein the irradiating the first tissue comprises irradiating an inclusion disposed in the first tissue with the first near infrared wavelength and ultrasound frequency.

21. The process of claim 17, further comprising:
acquiring, with the ultrasound transducer, an ultrasound echo frequency from the first tissue in response to the irradiating the first tissue with the ultrasound frequency; and
acquiring, with the first light detector, a first detected wavelength from the first tissue in response to the irradiating the first tissue with the first near infrared wavelength; and
processing the ultrasound echo frequency to produce morphology data of the inclusion.

22. The process of claim 19, further comprising using the optical property of the second tissue to produce functional data of the inclusion, the functional data comprising angiogenesis, hypoxia, optical absorption, oxygenated hemoglobin concentration, deoxygenated hemoglobin concentration, total hemoglobin concentration, oxygen saturation, or a combination comprising at least one of the foregoing properties.

23. The process of claim 22, further comprising displaying the morphology and functional data as an image of the inclusion.

* * * * *